United States Patent [19]

Matsumura

[11] 4,257,688
[45] Mar. 24, 1981

[54] EYE EXAMINING INSTRUMENT
[75] Inventor: Isao Matsumura, Yokosuka, Japan
[73] Assignee: Canon Kabushiki Kaisha, Tokyo, Japan
[21] Appl. No.: 906,081
[22] Filed: May 15, 1978
[30] Foreign Application Priority Data May 19, 1977 [JP] Japan ................................. 52-57941

[51] Int. Cl.³ .......................... A61B 3/14; A61B 3/10; G03B 29/00
[52] U.S. Cl. ......................................... 351/7; 351/6; 351/13; 354/62
[58] Field of Search ............... 356/153, 399, 4; 351/1, 351/6, 13, 16, 9; 350/2; 354/62

[56] References Cited
U.S. PATENT DOCUMENTS

| | | | |
|---|---|---|---|
| 3,536,384 | 10/1970 | Cocks | 351/13 X |
| 3,780,979 | 12/1973 | deGuillebon | 351/16 |
| 3,904,280 | 9/1975 | Tate | 351/1 |
| 3,915,564 | 9/1975 | Urban | 351/7 |

OTHER PUBLICATIONS

Kapany, "Fiber Optics Principles and Applications" 1967, pp. 171-174.

Primary Examiner—John K. Corbin
Assistant Examiner—Rodney B. Bovernick
Attorney, Agent, or Firm—Fitzpatrick, Cella, Harper & Scinto

[57] ABSTRACT

The instrument projects, to the anterior portion of a human eye, plural component beams images of which form a single mark image when said component beams are aligned, and inspects if said component images of the mark are aligned. The instrument is exactly positioned with respect to the human eye when said component images are aligned.

The mark image is observed through a finder of the instrument or by an infrared-visible image converter connected to the instrument, or it is refocused on and detected by photoelectric cells.

20 Claims, 22 Drawing Figures

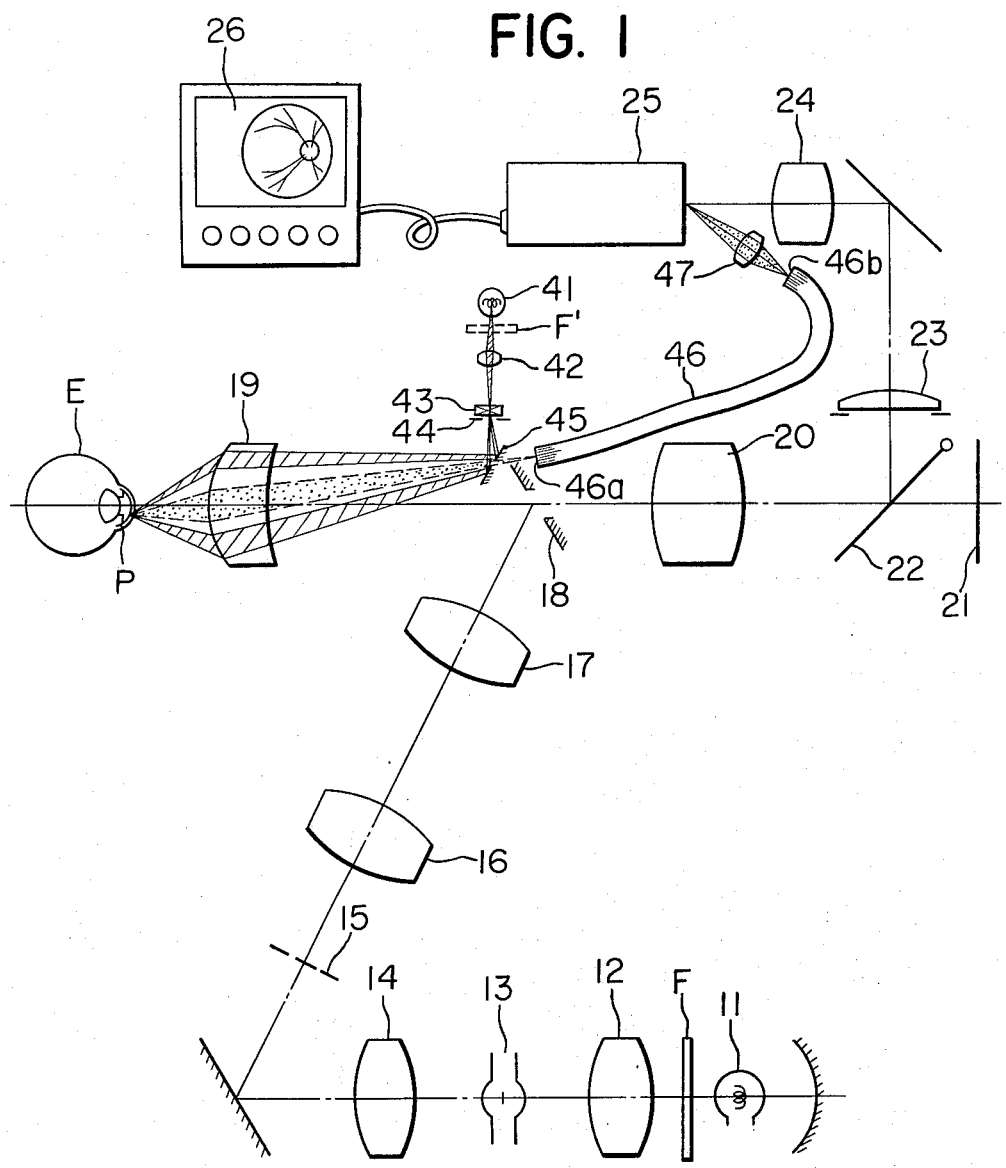
FIG. 1
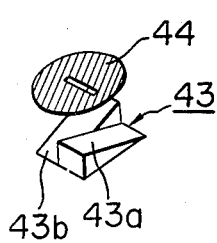
FIG. 2
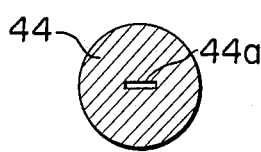
FIG. 3
FIG. 4
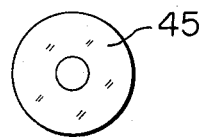
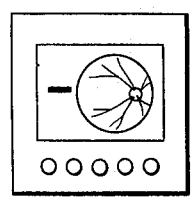
FIG. 5
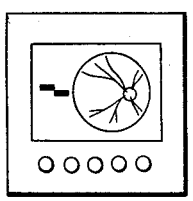
FIG. 6

EYE EXAMINING INSTRUMENT

BACKGROUND OF THE INVENTION

1. Field of the Invention

The present invention relates to an eye examining and testing instrument such as eye refractometer, retinoscope or eye fundus camera.

2. Description of the Prior Art

In such instrument a proper alignment or spacing with respect to the human eye is important for exact measurement or observation or for satisfactory photographing, since an incorrect alignment will result in erroneous measurement where a refractometer is used, or in a partial shielding of the photographing light beam by the iris of the eye where an eye fundus camera is used. On the other hand the spacing is usually predetermined structurally by the distance between the objective lens of the instrument and a support for stabilizing the face of the person to be inspected, but in case of the eye fundus camera the fundus illuminating light will be partly reflected by the cornea and mixed into the photographing light beam to form a flare in the image unless the working distance between the human eye and the objective lens is precisely adjusted. Also an exact spacing allows improvement in the accuracy of the instrument such as a refractometer.

In the comparison of aligning and spacing, an aligning process is rendered possible in many cases even with conventional instruments. For example in case of the eye fundus camera, the alignment is achieved by retracting the camera body from the human eye to focus the objective lens on the anterior portion of the eye, then adjusting the position of camera body in the vertical and horizontal directions in such a manner that the center of eye pupil coincides with the center of the viewing field of the finder and again returning the camera body to the original position. On the other hand an exact spacing has been very difficult to achieve.

U.S. Pat. No. 3,871,772 discloses a method of positioning of an eye examining instrument wherein the anterior chamber of the eye is uniformly illuminated by infrared light through the objective lens and is observed by a sight affixed on the instrument, and the adjustment of alignment and spacing is achieved by matching the center of the pupil with the center of a sight target plate. In this method, however, it is difficult to separate the aligning from the spacing.

SUMMARY OF THE INVENTION

The object of the present invention is to provide an eye examining instrument capable of detecting the optimum distance between the instrument and a human eye to be examined.

Another object of the present invention is to provide an eye examining instrument capable of positional detection without hindering the observation of the object portion of human eye by the observing system of the instrument.

Still other objects of the present invention will be made apparent from the following description of the embodiments of the present invention.

The instrument of the present invention is featured in that plural beams, each to be focused on a plane of a determined distance from the instrument, are projected onto the anterior portion of a human eye in such a manner that the central axes of said beams mutually cross, and a collective image thus formed on said portion is detected. In the following embodiments there is used a single mark as said collective image, but it is to be understood that plural marks may be equally employed for this purpose.

BRIEF DESCRIPTION OF DRAWINGS

FIG. 1 is a longitudinal cross sectional view of an embodiment of the present invention;

FIG. 2 is a perspective view showing a part of constituent members thereof;

FIGS. 3 and 4 are plan views of constituent members employed in the embodiment shown in FIG. 1;

FIGS. 5 and 6 are drawings each illustrating a display on a cathode ray tube;

DESCRIPTION OF THE PREFERRED EMBODIMENTS

Figure 7:
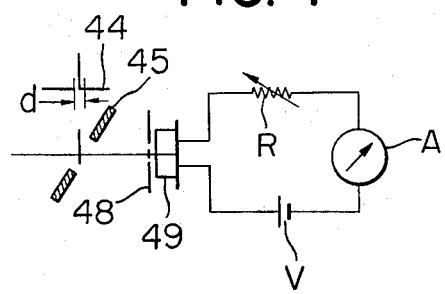
FIG. 7 is a partial cross sectional view showing a partial variation of the embodiment shown in FIG. 1.

Referring to FIG. 1 showing an embodiment of the present invention applied to an eye fundus camera, there are shown an eye E to be examined, a pupil P thereof, an observing light source 11 composed for example of a tungsten lamp, a detachable filter F intercepting the visible light and transmitting the infrared and near-infrared lights, a first condenser lens 12, a photographing light source 13 composed for example of a xenon tube, a second condenser lens 14, and a shield plate 15 provided with an annular aperture encircling a central light-shielding area. The light sources 11 and 13 are arranged in mutually conjugate positions with respect to the first condenser lens 12 while said light source 13 and the shield plate 15 are arranged in mutually conjugate positions with respect to the second condenser lens 14 whereby the beams emitted from said light sources 11 and 13 are focused on the annular aperture on said shield plate 15.

Further there are shown a relay lens groups 16, 17, an apertured mirror 18 provided with a central aperture which functions as a diaphragm for the photographing system to be explained later, said diaphragm being however realizable separately from said apertured mirror if desirable, and an objective lens 19. Said shield plate 15 and the pupil P of the eye E are positioned in approximately mutually conjugate positions with respect to the relay lens group 16, 17, the mirror surface of said apertured mirror 18 and the objective lens 19, and said pupil P is positioned conjugate with the diaphragm of the photographing system with respect to said objective lens 19.

The above-mentioned elements 11–19 constitute an illuminating system.

In FIG. 1 there are further shown an imaging lens group 20 for refocusing the image formed by said objective lens 19, and a photographic film 21 placed on the focal plane of said imaging lens group, whereby a photographing system is constituted by said objective lens 19, the aperture of said apertured mirror 18, the imaging lens group 20 and photographic film 21.

In FIG. 1 there are further shown a hoistable mirror 22 which is diagonally inserted on the optical axis between said imaging lens group 20 and photographic film 21 at the image observing operation and is retracted from said optical axis at the photographing operation, a field lens 23 in an approximately conjugate position with said photographic film 21 with respect to the mirror 22, a relay lens 24 for refocusing the image formed by said imaging lens group 20 onto the photosensitive surface of a pick-up tube 25 and a cathode ray tube 26 driven by the electric signal from said pick-up tube 25, the above-mentioned elements 22–26 constituting a finder system of the eye fundus camera.

Now there will be given an explanation on the beam projection system comprising a tungsten lamp 41, a condenser lens 42, a split prism 43 and a mark plate 44. Said split prism is of a structure as shown in FIG. 2, while said mark plate is provided with an oblong aperture 44a as shown in FIG. 3, or, instead, it may also be composed of a transparent plate coupled with a light-shielding member. The lengthwise direction of said oblong aperture 44a is parallel to the two surfaces 43a and 43b of said prism, of which crossing point coincides with the optical axis and is in conjugate relationship with the lamp 41 with respect to the condenser lens 42. The split prism 43 and the mark plate 44 are located very close to each other. 45 is a small apertured mirror the shape of which shape is represented as a plan view in FIG. 4.

As said mark plate 44 is, with respect to the small apertured mirror 45 and the objective lens 19, in conjugate relationship with an area of pupil P of the human eye E positioned at a predetermined distance, the beams emitted from said oblong aperture 44a of the mark plate, proceeding along two different directions, form an image the same as the original aperture on said area of pupil P. However, if the plane of the pupil is positioned closer or farther than said predetermined distance, said two beams representing a single mark image reach the pupil before or after reconstructing said image, thus producing a somewhat out-of-focus image of the aperture split into two at the center.

46 is a bundle of optical fibers for image transmission, of which input end 46a is positioned in conjugate relationship with the pupil at said predetermined distance with respect to the objective lens 9 while the output end thereof 46b is positioned in conjugate relationship with the pick-up tube or vidicon 25 with respect to a relay lens 47. In this embodiment said relay lens 47 is arranged in such a manner that the image obtained thereby does not overlap with the image produced by the relay lens 24. Also in case of an eye fundus camera without mydriasis, a pupil non-contracting beam is obtained by providing filters F and F' transmitting infrared and near-infrared light respectively in front of the lamps 11 and 41 and is used in combination with a pick-up tube sensitive to the infrared region.

Now an explanation will be given on the function of the instrument of the foregoing composition.

At first the objective lens 19 is positioned in front of the human eye to be examined, the lamp 41 is turned on, and the pick-up tube 25, cathode ray tube 26 and unrepresented processing circuit are switched on. The beam emitted by the lamp 41 is focused by the condenser lens 42 onto the split prism 43, and, after being divided into two beams by said prism 43, passes through the oblong aperture 44a of the mark plate. The two mark beams thus obtained are reflected by the apertured mirror 45 and focused at a predetermined distance by means of the objective lens 19. Upon reflection on the pupil, the beams pass through the objective lens 19 in the opposite direction and enter, through the aperture of the small apertured mirror 45, the input end 46a of the optical fiber bundle. The beams, upon transmission by said optical fiber bundle 46, are emitted from the output end thereof and focused, by means of the relay lens 47, onto the light-receiving face of the pick-up tube 25. Also when the lamp 11 is turned on, the image of the shield plate 15 is formed on the pupil of the human eye under examination to illuminate the eye fundus, and the reflected beam enters the pick-up tube through the objective lens 19, imageing lens group 20, hoistable mirror 22, field lens 23 and relay lens 24.

FIGS. 5 and 6 illustrate the examples of display on the cathode ray tube wherein the distance between the objective lens and the human eye satisfies a predetermined relationship in FIG. 5 while it does not in FIG. 6.

Thus the operator of eye fundus camera is capable, through watching the split mark image on the cathode ray tube, of spacing adjustment by moving the eye fundus camera forward or backward so as to restore the original shape of the mark. Also in case the eye E is not aligned with the objective lens 19, the image of the mark appears aberrated from the determined position.

FIG. 7 shows a partial variation of the foregoing embodiment wherein a small apertured mirror 45 corresponds to the one provided close to the apertured mirror 18 in FIG. 1, and in a conjugate position with the mark plate 44 with respect to said mirror there is provided a mask 48 behind which provided a light-receiving element 49. In this case the width d of the oblong aperture in the mark plate 44 is made equal to the width of light-shielding area between two apertures of the mask shown in FIG. 8. An indicating circuit including said light-receiving element is composed of an indicating meter A, a zero-adjust variable resistor R and a battery V, and an indication corresponding to the quantity of light transmitting said mask is obtained by employing a light-receiving element, such as CdS element, capable of controlling the electric current therethrough in response to the quantity of received light.

Figures 8, 9, 10:
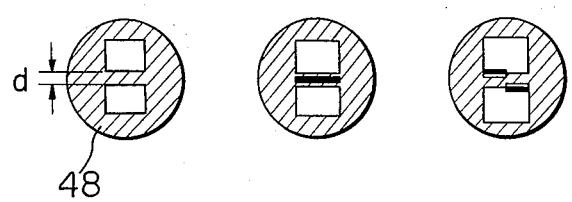
FIG. 8 is a plan view of a constituent member employed therein.
FIGS. 9 and 10 are drawings illustrating the function of the variation shown in FIG. 7.

In this variation the light-receiving element 49 does not receive light if the pupil of the human eye under examination is located at the predetermined position since the image of the mark is formed on said light-shielding area of the masks as shown in FIG. 9. However, in case the pupil is displaced from said predetermined position, the image of the mark becomes split from the center to be displaced from said light-shielding area, thus causing entry of light into the element 49 and giving an indication on the ammeter. The operator of the eye fundus camera is therefore capable of achieving the adjustment of spacing by moving the camera forward or backward, watching the indication on the ammeter.

Figure 11:
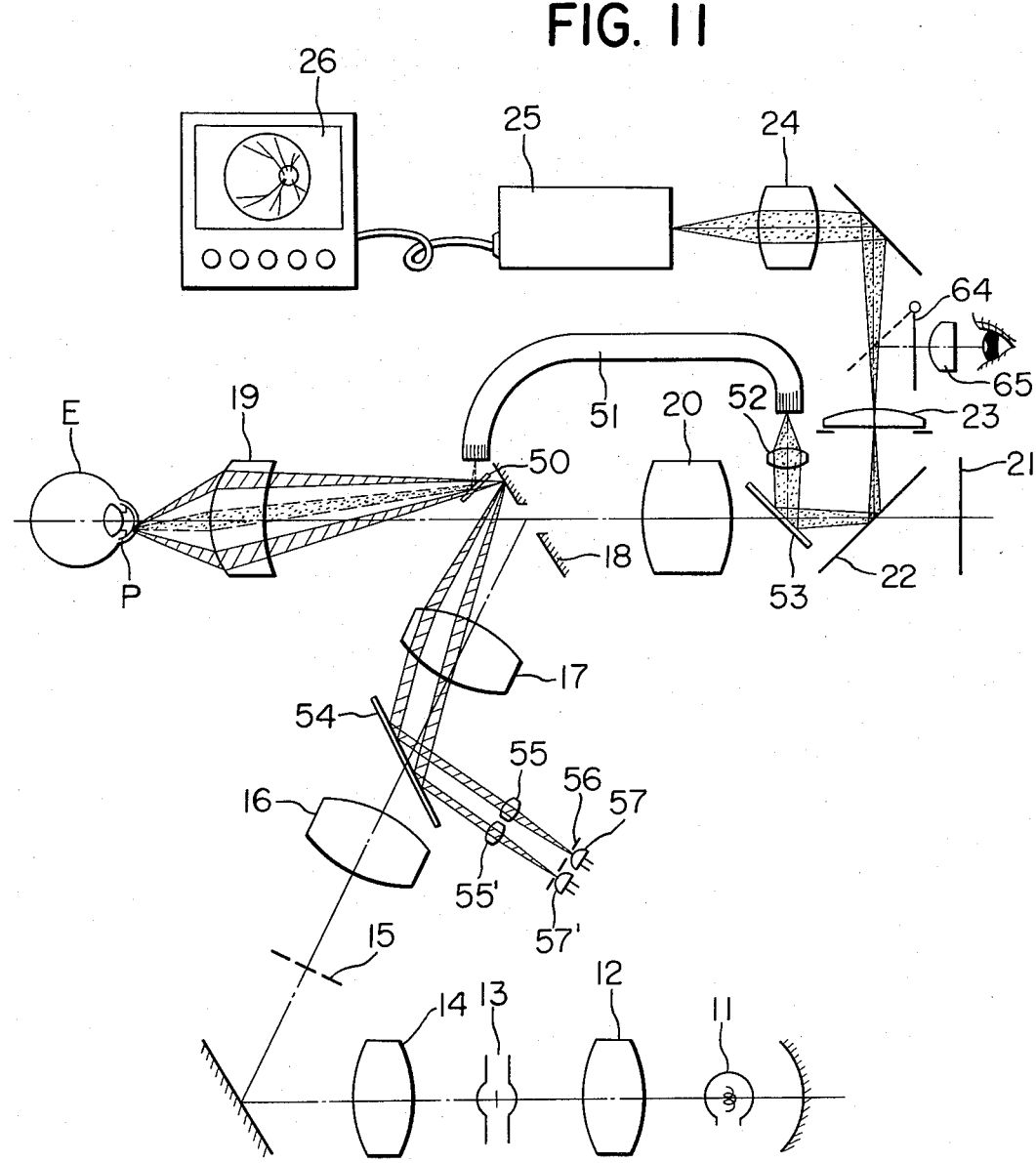
FIG. 11 is a longitudinal cross sectional view of an another embodiment of the present invention.

FIG. 11 shows an another embodiment of the present invention, wherein the same components as in FIG. 1 are given same numbers. In FIG. 11 there are further shown a semi-transparent mirror 50, an optical fiber bundle 51 for image transmission which may be replaced by an optical guide system composed of lenses and mirror if desirable, a relay lens 52 and a semi-transparent mirror 53 displaceable in a direction perpendicular to the paper plane.

Figure 12:
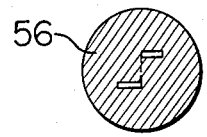
FIG. 12 is a plan view of a constituent member to be employed therein.

There are further shown light-emitting diodes 57, 57', a mark plate 56 provided with two slits of a shape as if a single slit is split in the center as shown in FIG. 12, said light-emitting diodes being respectively provided behind said slits, relay lenses 55, 55' of mutually parallel optical axes of which focal plane is located at said mark plate 56 thereby to obtain parallel light beams from said lenses, and a semi-transparent mirror 54 provided diagonally on the optical axis between the relay lenses 16 and 17 to direct the light beams from said relay lenses 55, 55' toward the relay lens 17. Since the apertured mirror 18 is positioned on the focal plane of said relay lens 17, the images formed by the beams from said mark plate 56 are connected as a single line on said apertured mirror. Upon reflection on said mirror, said beams are again separated and focused by the objective lens 19 to again form a connected single slit image at a predetermined position. Upon reflection by the pupil P, said beams are focused by the objective lens 19 and reflected by the semi-transparent mirror 50 to enter the optical fiber bundle 51. After transmission therethrough the beams emitted from said optical fiber bundle are guided to the pick-up tube through the relay lens 52, semi-transparent mirror 53, hoistable mirror 22, field lens 23 and relay lens 24.

Figure 13:
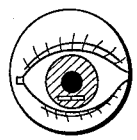
FIGS. 13 and 14 are drawings of a human eye under observation on which a mark is projected.
Figure 14:
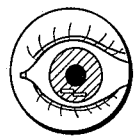

FIGS. 13 and 14 illustrate the states of human eye under examination on which the mark is projected, wherein FIG. 13 shows the formation of a single slit on the pupil when the eye and the objective lens satisfy a predetermined relationship while FIG. 14 shows the formation of split slits when said relationship is not satisfied.

Figure 15:
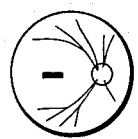
FIGS. 15 and 16 are drawings illustrating a display on a cathode ray tube.
Figure 16:
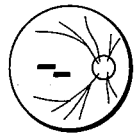

The states of the eye shown in FIGS. 13 and 14 are respectively displayed on the cathode ray tube 26 as shown in FIGS. 15 and 16. Thus the operator of the eye fundus camera is capable, when observing a split image display on the cathode ray tube as shown in FIG. 16, of adjusting the spacing by moving the camera forward or backward so as to obtain a connected single slit image. When the tungsten lamp 11 is turned on during said adjustment, an annular image of the annular aperture of the shield plate 15 is formed in the vicinity of the pupil to illuminate the eye fundus, and the reflected light is guided through the objective lens 19, imaging lens group 20, semi-transparent mirror 53, hoistable mirror 22, field lens 23 and lens 24 to form an image of the eye fundus on the pick-up tube 25 which is also shown on the above-mentioned display.

Figure 17:
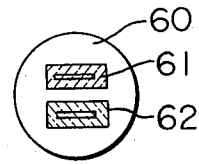
FIG. 17 is a plan view showing a variation of the mark plate.

FIG. 17 shows another form of mark plate 60 provided with two parallel slits respectively provided with filters 61, 62 of complementary colors. When such mark plate 60 is inserted in place of the aforementioned mark plate 56 and the image on the field lens 23 is viewed with a mirror 64 diagonally inserted into the optical axis and through an eyepiece lens 65, the operator will observe lines of two colors if the aforementioned relationship is not satisfied while said colors vanish when said relationship is satisfied.

Figure 18:
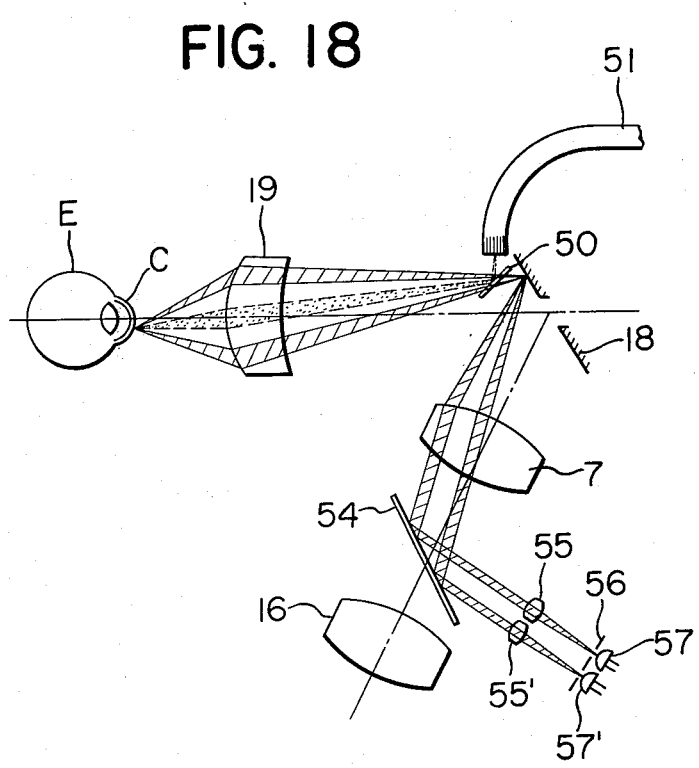
FIG. 18 is a partial cross sectional view of a variation of the embodiment shown in FIG. 11.

FIG. 18 shows a still another embodiment of the present invention, details of which are not explained as the composition thereof is more or less similar to that shown in FIG. 11. In this embodiment the image of the mark plate 56 is projected through the objective lens onto a portion excluding the summit portion of the cornea C in order to utilize the scattering property thereof of the human eye E. It is also possible to utilize the mirror reflection by projecting said image onto the summit portion of the cornea C.

Figure 19:
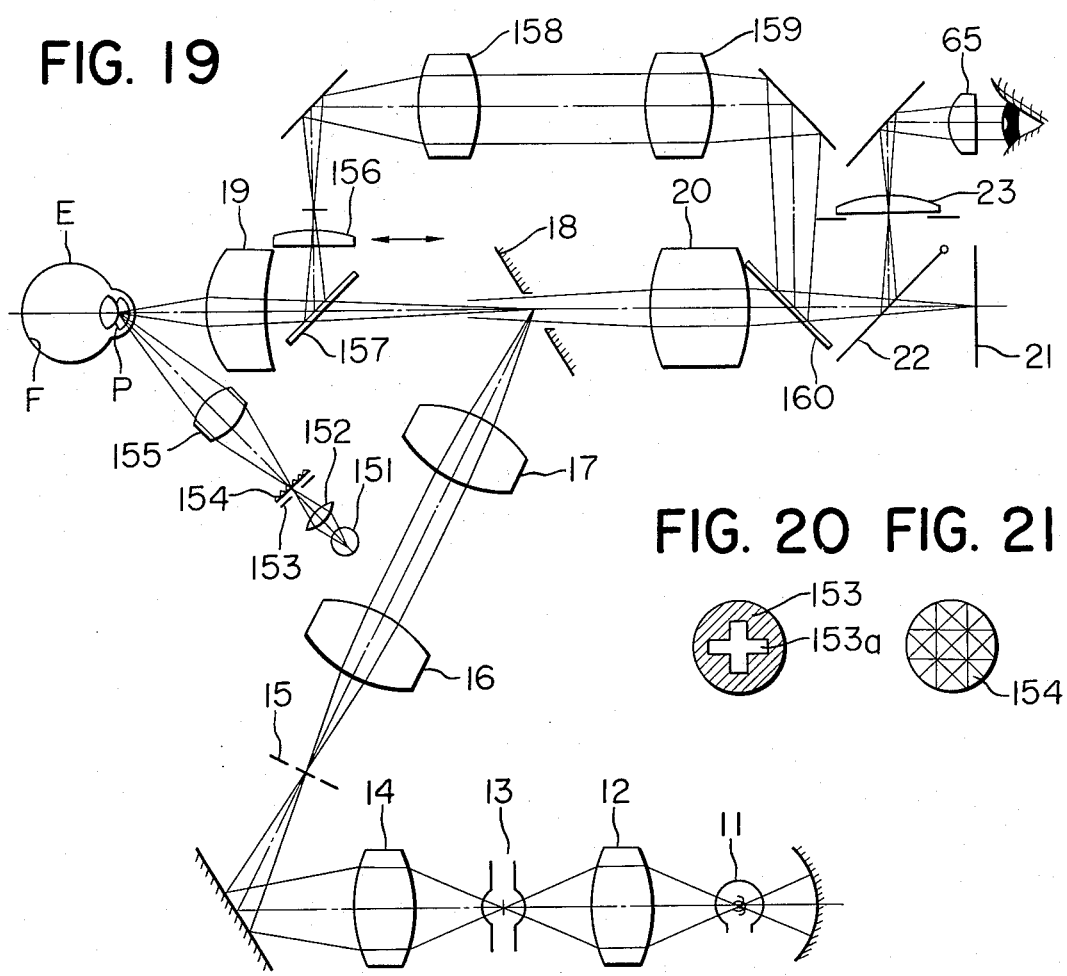
FIG. 19 is a longitudinal cross sectional view of a still another embodiment of the present invention.
Figures 20, 21:
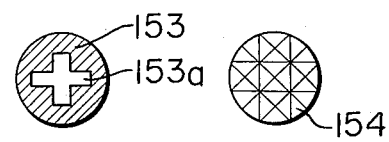
FIGS. 20 and 21 are plan views of constituent members to be employed therein.

FIG. 19 shows still another embodiment of the present invention wherein the mark projecting beam is diagonal with respect to the optical axis of the objective optical system for the principal function of the eye examining instrument, and the reflected beams are received by said objective optical system. In FIG. 19 there are shown a tungsten lamp 151, a condenser lens 152, a mark plate 153 provided with a slit of a shape shown in FIG. 20, a micro-prism plate 154 the shape of which is represented in plan view in FIG. 21, a projecting lens 155 for maintaining said mark plate 153 with conjugate relationship with a determined area of the pupil P of the human eye located at a predetermined position, a focusing lens 156 displaceable in the direction of the arrow to form, by means of said lens 156 and the objective lens 19, an image of the pupil in a position where the image of the eye fundus is formed by means of the objective lens 19 alone, semi-transparent mirrors 157, 160 retractable in a direction perpendicular to the paper plane, and relay lenses 158, 159 for forming an image of the pupil on the position of a photographic film. A photographing system is composed of the objective lens 19, imaging lens group 20 and photographic film 21, while a finder system is composed of the hoistable mirror 22, field lens 23, a diverging mirror and an eyepiece lens 65.

In the above composition the tungsten lamp 151 illuminates the mark plate 153 through the condenser lens 152, and the beam passing through the slit 153a is diverted into four directions by means of the microprisms and again focused by the projecting lens 155 to a predetermined position to reproduce the shape of slit 153a. These beams are scattered by the pupil P of the eye under examination, then focused on the field lens 23 through the objective lens 19, semi-transparent mirror 157, focusing lens 156, relay lenses 158, 159, semi-transparent mirror 160 and hoistable mirror 22 and viewed through the eyepiece 65.

Thus the operator can confirm the shape of slit 153a on the pupil if the distance between the eye E under examination and the objective lens 19 satisfies a predetermined relationship but merely observes a deformed slit image if said relationship is not satisfied. The operator is therefore capable of adjusting the spacing by moving the camera forward or backward so as to find a position where said slit image is reconstructed. Furthermore the operator is capable of simultaneously observing the image of the eye fundus through the objective lens 19, imaging lens group 20, hoistable mirror 22, field lens 23 and eyepiece lens 23.

Figure 22:
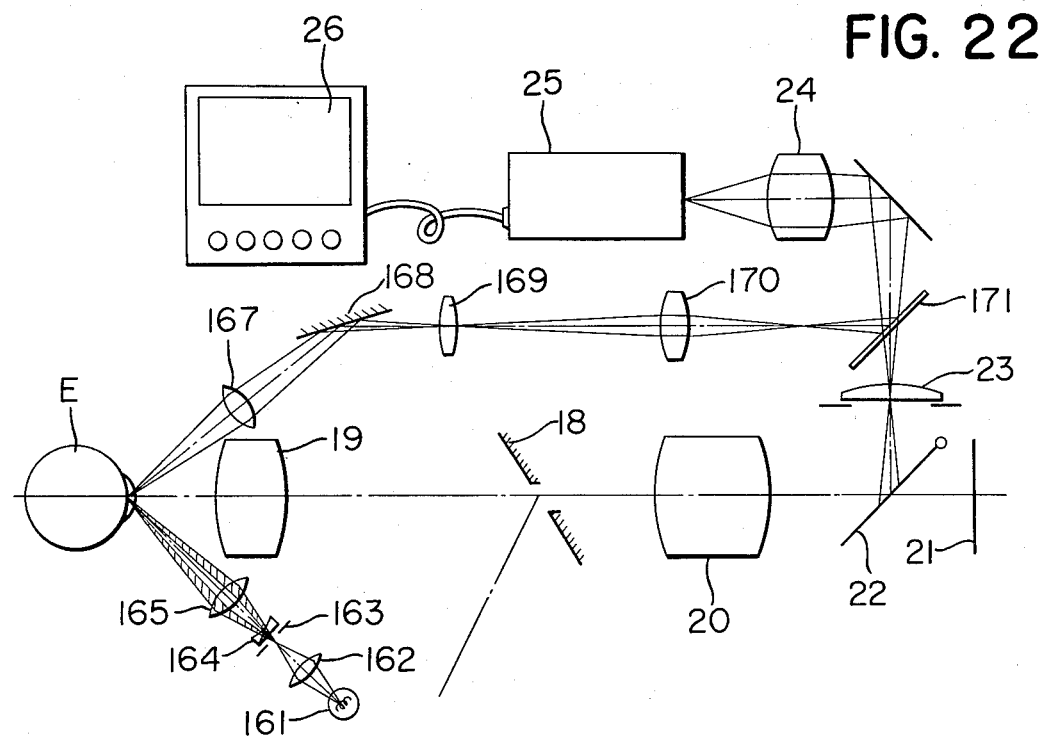
FIG. 22 is a longitudinal cross sectional view of a still another embodiment of the present invention.

FIG. 22 shows still another embodiment of the present invention wherein a mark projecting system and an optical system for receiving the reflected beam are provided diagonally with respect to the optical axis of the objective optical system positioned in facing relationship with the eye under examination, and the reflected light received by said receiving optical system is guided through a transmitting optical system to the observing system for the principal function of the eye examining instrument. Thus the arrangement of the objective lens 19, apertured mirror 18, imaging lens group 20, hoistable mirror 22, photographic film 21, field lens 23, relay lens 24, pick-up tube 25 and cathode ray tube 26 is identical to that in the foregoing embodiments. The illuminating system is omitted for clarity.

In FIG. 22 there are further shown a tungsten lamp 161, a condenser lens 162, a mark plate 163 provided with a slit extended in the horizontal direction, a prism 164 similar to the split prism 43 shown, in FIG. 2, and a projecting lens 165. The mark plate 163 is in conjugate relationship with a determined area to the objective lens of the sclera of the eye E under examination with respect to said projecting lens. There are further shown a light-receiving lens 167 directed toward said determined area, a mirror 168 to divert the direction of the beam passing through said lens 167, a field lens 169 provided in conjugate relationship with said determined area with respect to the lens 167, a relay lens 170 for refocusing the image formed by said lens 167, and a semi-transparent mirror 171 for introducing the beam emitted by said relay lens 170 into the observing system.

In the above-explained composition, the light emitted by the lamp 161 is concentrated on the slit of the mark plate 163 by means of the condenser lens 162, and the beam passing through said slit is split, by means of the split prism 164, into two beams which are focused in a predetermined position by means of the projecting lens 165. The beams reflected by the sclera of the eye under examination are collected by the lens 167, reflected by the mirror 168 and focused on the field lens 169, and the resulting image is again focused by the relay lens 170, reflected by the semi-transparent mirror 171 and transmitted by the relay lens 24 to the light-receiving face of pick-up tube 25. Thus the display on the cathode ray tube 26 shows an image of the slit, in a form of a single line or in a form split in the center respectively when the eye under examination is in or out of the predetermined position. Further in the present embodiment it is also possible to project the mark onto the pupil or cornea in order to utilize the scattering reflection thereof. Also if the optical axes of the projecting system and of the lens 167 are arranged symmetrical with respect to the optical axis of the objective lens 19, it is possible to project the mark in the vicinity of the summit of cornea in order to utilize the mirror reflection thereof.

What I claim
1. An image examining instrument comprising:
an eye inspecting system;
a mark;
a prism for splitting an image of the mark into plural mark images;
a beam projection system for projecting beams for forming an image of the mark at an anterior portion of the eye;
imaging optical means, directed at the anterior portion of the eye for imaging the beams reflected by said anterior portion; and
a mark detecting system for detecting the positions of a plane which is in conjugate relationship with said anterior portion of the eye with respect to said imaging optical means, said mark and said prism being so arranged that when positioning of the eye and instrument is correct, the mark images are aligned.

2. An eye examining instrument according to claim 1 wherein said mark detecting system comprises an image display system and an image transmitting system for transmitting the image of said marks to said image display system.

3. An eye examining instrument according to claim 2 wherein said image transmitting system comprises a bundle of fibers and lens means.

4. An eye examining instrument according to claim 2 wherein said image transmitting system comprises plural lens groups.

5. An eye examining instrument according to claim 2 wherein said image display system comprises a pick-up tube and a cathode ray tube.

6. An eye examining instrument according to claim 1 wherein said mark detecting system comprises a photoelectric device and display means operated by the output of said photoelectric device.

7. An eye examining instrument according to claim 6 wherein said photoelectric device comprises a photoelectric cell and masking means provided in front thereof.

8. An eye examining instrument according to claim 1 wherein said eye inspecting system comprises objective lens means provided in facing relationship with the eye to be examined.

9. An eye examining instrument according to claim 8 wherein said eye inspecting system comprises an image forming lens group, an observing system and an illuminating system provided on the image side of said objective lens means.

10. An eye examining instrument according to claim 9 wherein said observing system comprises at least a lens group, a pick-up device and a display device.

11. An eye examining instrument according to claim 9 wherein said eye inspecting system is provided with a photographic film behind said image forming lens group.

12. An eye examining instrument according to claim 1 wherein said eye inspecting system, said beam projection system and said imaging optical means are provided in common with objective lens means arranged in facing relationship with the eye to be examined.

13. An eye examining instrument according to claim 1 wherein an optical axis of said beam projection system intersects an optical axis of said eye inspecting system.

14. An eye examining instrument comprising:
an eye inspecting system adapted to be focused on a fundus of an eye to be inspected;
observation means for observing an image surface of said eye inspecting system;
a mark projection system for projecting plural beams each forming an image of a mark and mutually joining at the anterior portion of the eye and arranged at a predetermined position;
receiving optical means, adapted to oppose the eye, for receiving the images of the marks reflected by the anterior portion of the eye; and
image transmitting means, optically coupled with said receiving optical means, for transmitting images of marks to said observation means, wherein when positioning of said eye and said instrument is correct, the images of the marks are aligned in said observation means.

15. An instrument according to claim 14, wherein said mark projection system projects the beams through said receiving optical means.

16. An instrument according to claim 14, wherein said eye inspecting system comprises an objective lens adapted to oppose the eye to be inspected, an image forming lens arranged co-axially with said objective lens, an aperture stop disposed between said objective lens and said image forming lens and illuminating means for illuminating said eye fundus, wherein said mark projection system projects the beams through said objective lens.

17. An instrument according to claim 14, wherein said eye inspecting system comprises an objective lens adapted to oppose the eye to be inspected, an image forming lens arranged co-axially with said objective lens, an aperture stop disposed between said objective lens and said image forming lens, photosensitive means for receiving an image of the fundus of the eye formed by said image forming lens, and illuminating means for illuminating said eye fundus, and wherein said objective lens functions also as said imaging lens.

18. An instrument according to claim 14, wherein said image transmitting means includes a bundle of optical fibers.

19. An instrument according to claim 14, wherein the image of the eye fundus and the images of the marks appear side by side in said observation means.

20. An instrument according to claim 14, wherein the image of the eye fundus and the images of the marks occur in superposed relationship.

* * * * *